United States Patent [19]
Richelsoph

[11] Patent Number: 5,863,293
[45] Date of Patent: Jan. 26, 1999

[54] SPINAL IMPLANT FIXATION ASSEMBLY

[75] Inventor: Marc Richelsoph, Memphis, Tenn.

[73] Assignee: Spinal Innovations, Cordova, Tenn.

[21] Appl. No.: 734,520

[22] Filed: Oct. 18, 1996

[51] Int. Cl.⁶ .................................................. A61B 17/56
[52] U.S. Cl. .............................................. 606/61; 606/73
[58] Field of Search ........................................ 606/61, 73

[56] References Cited

U.S. PATENT DOCUMENTS

| | | | |
|---|---|---|---|
| 5,217,497 | 6/1993 | Mehdian ..................................... | 606/61 |
| 5,257,993 | 11/1993 | Asher et al. ................................ | 606/61 |
| 5,443,467 | 8/1995 | Biedermann et al. ...................... | 606/73 |
| 5,476,464 | 12/1995 | Metz-Stavenhagen et al. .......... | 606/73 |
| 5,549,608 | 8/1996 | Errico et al. ............................... | 606/73 |
| 5,554,157 | 9/1996 | Errico et al. ............................... | 606/73 |
| 5,586,984 | 12/1996 | Errico et al. ............................... | 606/61 |
| 5,669,911 | 9/1997 | Errico et al. ............................... | 606/73 |

FOREIGN PATENT DOCUMENTS

| | | | | |
|---|---|---|---|---|
| 2682280 | 4/1993 | France | ..................... | 606/61 |

*Primary Examiner*—Michael Buiz
*Assistant Examiner*—Julian W. Woo
*Attorney, Agent, or Firm*—Kohn & Associates

[57] ABSTRACT

A spinal implant fixation assembly includes a bone fixation member, such as a screw or hook for fixation to a bone. A rod receiving seat is operatively connected to the bone fixation element for seating a portion of a rod therein. A locking mechanism, in the form of a nut and locking ring engage the rod receiving seat for forcing an inner wall of the rod receiving seat to contour around and engage the rod seated therein and for locking and fixing the rod relative to the inner housing. In one embodiment, the locking ring secures a head portion of the bone fixation element within the assembly. A method is also provided for locking the rod to a bone by fixing a rod seating member to a bone and seating a portion of a rod within a substantially U-shaped seat of the seating member. The rod is then locked within the U-shaped seating member while engaging and contouring at least a portion of the U-shaped seat about the rod.

17 Claims, 2 Drawing Sheets a implant fixation system and locking mechanism. More particularly, the present invention provides a locking mechanism, which can be multi-planar or fixed, for securing a rod to an implant.

SPINAL IMPLANT FIXATION ASSEMBLY

TECHNICAL FIELD

The present invention relates to a implant fixation system and locking mechanism. More particularly, the present invention provides a locking mechanism, which can be multi-planar or fixed, for securing a rod to an implant.

BACKGROUND OF THE INVENTION

Stabilization of the spine for various conditions, including degenerative disc disease, scoliosis, spondylolithises and spinal stenosis often require attaching implants to the spine and then securing the implants to spinal rods. Such spinal fixation devices can immobilize the vertebrae and can alter the alignment of the spine over a large number of vertebrae by means of connecting at least one elongate rod to the sequence of selected vertebrae. Such rods can span a large number of vertebrae, such as three or four. However, the spine anatomy rarely allows for three or more implants to be directly in line. In order to allow for this irregularity, the rod must be contoured to the coronal plane. With anatomical curvature in the saggital plane found in the lumbar spine, the rod has to be contoured in both planes, requiring considerable effort and surgical time.

For example, the U.S. Pat. Nos. 5,554,157, issued Sep. 10, 1996, and 5,549,608 issued Aug. 27, 1996, both to Errico et al. disclose polyaxial locking screw and coupling element devices for use with rod fixation apparatus. The '157 patent discloses a coupling element including an interior axial passage having an interior surface which is inwardly curvate at the lower portion thereof such that it comprises a socket for polyaxially retaining a spherical head of a screw. The coupling element further includes a pair of vertically oriented opposing channels extending down from the top of the coupling element which define therebetween a rod receiving seat. The channel further provides the walls of the upper portion to a pair of upwardly extending members, each including an exterior threading disposed on the upper most portion thereof for receiving a locking nut. During the implantation of the assembly, the locking nut seats against the top of the rod which in turn seats on top of the screw head. The nut causes the rod to be locked between the nut and screw and the screw to be locked in the socket.

The '608 patent discloses a modification wherein a locking ring is disposed about the exterior of the lower portion of the coupling element and provides an inward force on an outwardly tapered portion upon downward translation thereof causing the interior chamber to crush lock a screw head therein to eliminate the polyaxial nature of the screw element coupling.

In both prior art embodiments, the locking mechanism locks both the rod and screw head simultaneously. No prior art patent allows for the spherical head of the screw to be locked at a desired angle prior to rod insertion. Likewise the only surface locking the rod in place is the surface between either the seat and a locking nut or the rod entrapped between a locking ring and the seat.

It would be desirable to increase the area of contact of the locking mechanism about the rod as this is a high stress site secured only by a friction fit. It would also be desirable to lock the screw head in place prior to fixation of the rod.

SUMMARY OF THE INVENTION

In accordance with the present invention, there is provided a spinal implant fixation assembly including bone fixation means for fixation to a bone and rod receiving means operatively connected to the bone fixation means. The rod receiving means includes a first seat having an inner wall for seating a portion of a rod therein. The assembly further provides locking means engaging the rod receiving means for forcing the inner wall to contour around and engage the rod seated therein and for locking and fixing the rod relative to the inner housing.

The present invention further provides a method for locking a rod to a bone by the steps of fixing a rod seating member to a bone and then seating a portion of a rod within a substantially U-shaped seat of the seating member. The rod is locked within the U-shaped seat while engaging in contouring at least a portion of the U-shaped seat about the rod.

BRIEF DESCRIPTION OF THE FIGURES

Other advantages of the present invention will be readily appreciated as the same becomes better understood by reference to the following detailed description when considered in connection with the accompanying drawings wherein.

DETAILED DESCRIPTION OF THE FIGURES

Figure 1:
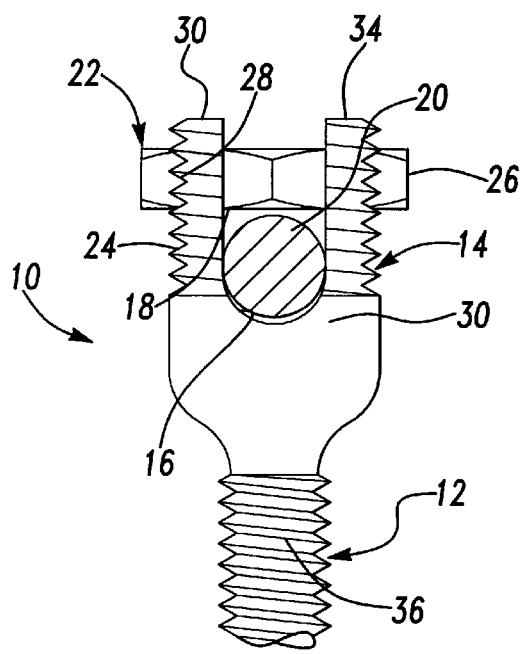
FIG. 1 is a side view partially in cross section of a first embodiment of the present invention.

A spinal implant fixation assembly constructed in accordance with the present invention is generally shown at 10 in FIG. 1. Similar structures amongst the several embodiments are shown by primed numbers in the various Figures.

More specifically, referring to the first embodiment of the present invention generally shown at 10 in FIG. 1, the assembly 10 includes a bone fixation element generally shown at 12 for fixation of the assembly 10 to a bone. A rod receiving mechanism is generally shown at 14 and is operatively connected to the bone fixation element 12. The rod receiving mechanism 14 includes a seat 16 having an inner wall 18 for seating a portion of a rod 20 therein. A locking mechanism generally shown at 22 engages the rod receiving mechanism 14 for forcing the inner wall 18 to contour around and engage the rod 20 seated therein and for locking and fixing the rod 20 relative to the assembly 10. In this manner, as the locking mechanism 22 forces the inner wall 18 to contour around and engage the rod 20 seated therein, there is increased surface to surface contact and therefore increased frictional engagement between the seat 16 and rod 20 thereby providing a more effective frictional contact. That is, the inner wall 18 of the seat 16 is compressed against the rod 20. The locking mechanism 22 is also seated against the rod 20. However, unlike prior art assemblies discussed above, the surface area engaging against the rod 20 is vastly increased over the prior art which increases the assembly to rod holding power.

More specifically, the rod receiving mechanism 14 includes a tapered outer surface 24. As shown in the several embodiments, this outer surface 24 can be threaded. However, other means for securing the locking mechanism 22 can be used to achieve the same results. Preferably, the locking mechanism 22 is in the form of a nut member 26 having an inner surface 28, which can be threaded for use with the threaded outer surface 24 of the rod receiving mechanism 14, for being forced over and engaging the outer surface 24 and inwardly deflecting the rod receiving mechanism 14 about the seat portion 16 as the locking member 26 further engages the tapered outer surface 14.

Referring more specifically to the rod receiving mechanism 14, it includes a body portion 30 having two arms 32,34 extending therefrom and being substantially parallel relative to each other. The two arms 32,34 and the body portion 30 form a U-shaped inner surface defining the seat portion 16 thereof. Also, the arms 32,34 have the tapered threaded surface 24 about the outer surface thereof. Thus, as the locking mechanism 22 in the form of the nut member 26 is threaded over the tapered outer surface 24 of the arms 32,34, the nut member 26 compresses the arms 32,34 against a rod member 20 disposed within the seat 16. As stated above, this provides a vastly increased surface area engagement between the seating surface 16, inner walls 18 and rod member 20. The arms 32,34 provide for flexibility, yet are sufficiently rigid to maintain structural integrity.

The tapered threaded portion 24 in combination with the nut member 26 provide a self-locking mechanism for securing the rod 20 thereto. By self-locking, it is meant that mere threading of the nut member 26 on the tapered surface 24 locks the nut member 26 in place. This locking mechanism is vibration resistant and has not been previously used in spinal implants. In combination with the other aspects of the present invention, the self-locking mechanism provides convenience of use and secure locking of the system along with flexibility of attachment of the rod and implant.

Figure 2:
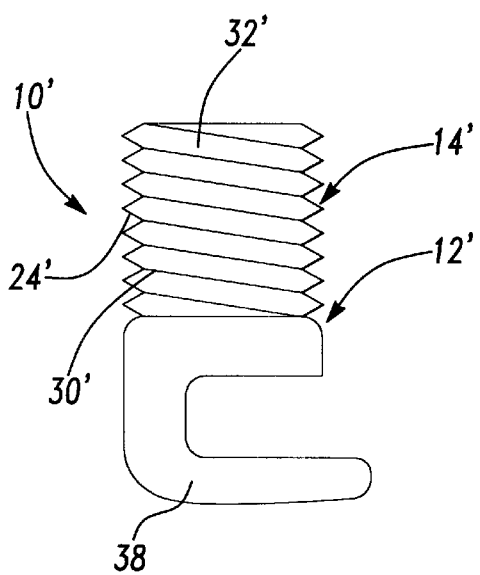
FIG. 2 is a side view of a second embodiment of the present invention.

In the first embodiment shown in FIG. 1, the bone fixation mechanism 12 is shown as a screw portion 36 extending integrally from the body portion 30. The body portion 30 includes a longitudinal axis. The bone fixation element 12, whether it is a screw portion as shown in FIG. 1 at 36 or a hook portion 38 as shown in FIG. 2, can either 1) lie along the axis so as to define a substantially linear element or 2) be angled relative to the longitudinal axis of the body portion 30. In this manner, the device can be adapted to various angulations between the bone connection surface and the rod 20. These embodiments of the invention provide either a thread or hook portion 36,38, respectively, having the upper tapered threaded portion about the U-shaped seat 16. Variability of angulation is eliminated as each unit would be a solid fix piece. But the assemblies can be individually made in various angulations. Such assemblies provide solid fixation of implants to the rod 20 where angulation is either not required or where known angulation may be repeatedly needed.

As stated above, the bone fixation element 12 can take on various shapes and sizes known in the art. The element 12 can have various configurations as a screw 36 and various thread designs. Also, as shown in FIG. 2, the hook portion 38 can be manufactured and used in a variety of hook sizes. Other shapes and sizes well known in the art can also be used.

The assembly is preferably made from machined titanium or alloy, but can be alternatively made from other types of cast or molded materials well known in the art.

Figure 3:
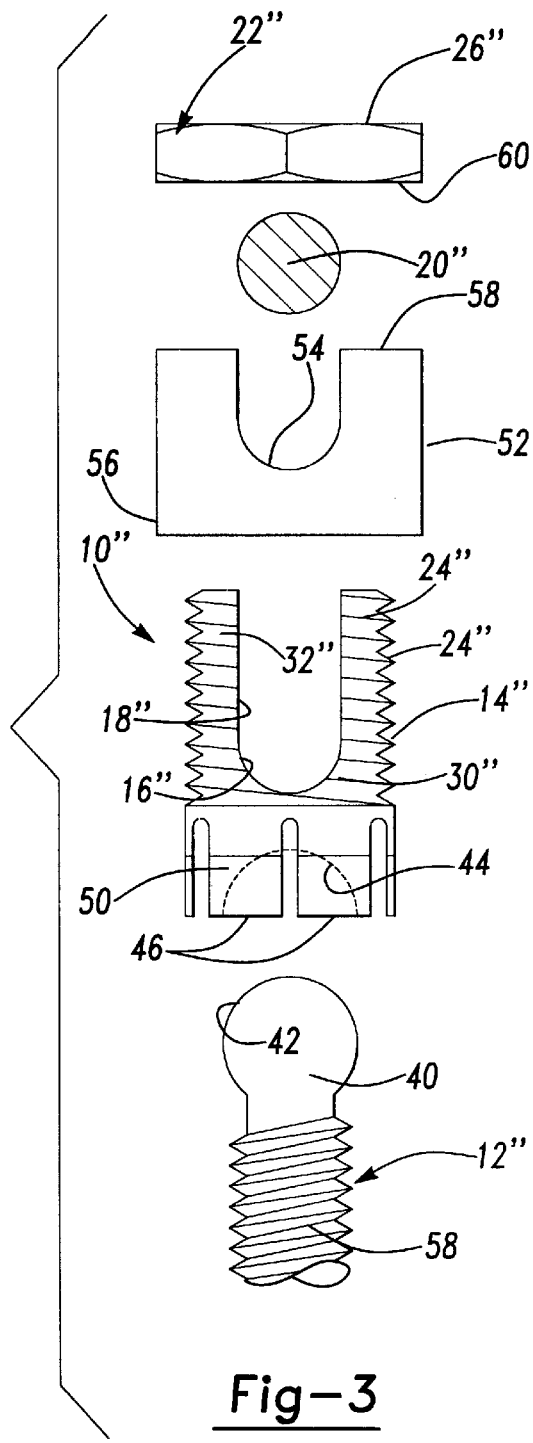
FIG. 3 is a side exploded view of a third embodiment of the present invention.
Figure 4:
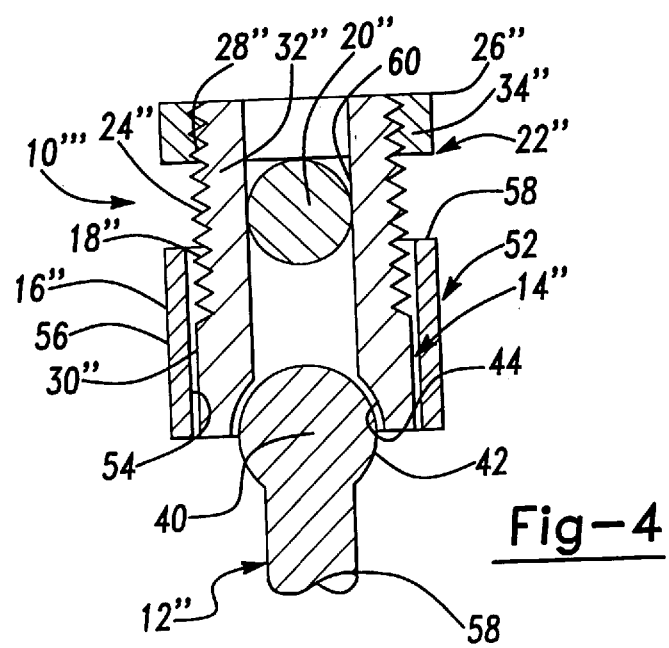
FIG. 4 is a cross sectional side view of the third embodiment of the present invention as assembled.

A second alternative embodiment of the present invention is shown in FIGS. 3 and 4. As stated above, double primed numbers are used to indicate like structure between the several embodiments.

Referring specifically to FIGS. 3 and 4, the bone fixation element 12" is shown as an independent screw member. The element 12" includes a head portion 40 having a substantially spherical outer surface 42. The rod receiving mechanism 14" is shown as a single integral unit including the first seat 16" for receiving the rod member 20" as discussed above between the arms 32" and 34" and a second seating surface 44 having a substantially spherical shape for seating the head portion 40 of element 12" therein.

Referring more specifically to the rod receiving member 14", it consists of a substantially tubular body including the pair of spaced substantially parallel arms 32",34" extending therefrom and forming the substantially U-shaped seat 16" as discussed above. The tubular body further includes a socket portion defining the second seat 44 which includes outwardly flaring flanges 46, as best shown in FIG. 3. The outwardly flaring flanges 46 have distal ends which flare radially outwardly relative to a central axis of the rod receiving member 14. The outer surfaces 50 define the outer surface of the second seat 44.

The locking mechanism 22" of this embodiment includes the nut member 26" and a tubular sleeve member generally shown at 52. Although the nut member 26" and sleeve member 52 are shown as separate elements, the present invention could be practiced where the nut member 26" includes a skirt portion integrally extending therefrom. In either embodiment, the sleeve 52 locks and fixes the head portion 40 of the screw element 12" within the seat 44 prior to the nut member 26" locking and fixing the rod 20" within the seat 16". The sleeve member 52 includes an inner surface 54 which, upon being disposed over and about the outer surface 50 of the flanges 46, engages and inwardly deflects the distally outwardly tapering surfaces thereof to engage the socket portion of the seat 44 with the head portion 40 of the screw member 12". This can be accomplished prior to the connection of member 14" with the rod 20" and its locking in place by the nut member 26".

Referring more specifically to the sleeve member 52, it includes curved recessed portions 54 for seating of the rod member 20" therein in the assembled configuration as shown in FIG. 4. The sleeve 52 also includes a skirt portion 56 which is disposed about the flanges 46 in the assembled position, as shown in FIG. 4. In the embodiment shown in FIGS. 3 and 4, the element 30" includes the tapered threaded outer surface 24" which can be engaged by the threaded inner surface 28" of the nut member 26". As the nut member 26" is threaded over the outer tapered surface 24", it not only inwardly deflects the arms 32",34" to engage the rod member 20" but also forces the skirt portion 56 of the sleeve member 52 over the outwardly flared flanges 46 so as to force the inner surface of the seat 44 to frictionally engage and hold in place in a fixed manner the head portion 40 of the screw element 12". The screw element 12" is then locked securely at whatever angle the components are in. This locking is independent of the locking of the rod 20" in place.

This locking of the screw element can occur in two ways. The outer sleeve 52 can be pushed down with an instrument without the rod being in place or pushed down as the nut 26" is tightened over the rod 20". This gives the surgeon the option of adjusting the screw angle for abnormal anatomy and locking it prior to locking the rod 20" to the assembly 10" or, alternatively, locking the screw element 12" and rod 20" interfaces simultaneously when correction is not required.

As stated above, the head portion 40 is shown to be substantially spherical in shape. The seat 44 is a socket portion which is also substantially spherical for seating and engaging the head portion 40 therein. This allows for easy angular adjustment between the two components.

Alternatively, the head portion 40 of the screw element 12" can take on various other shapes, such as a square shape, which may not allow for similar angulation but would allow for similar connection between the head portion 40 and the seat 44 in accordance with the present invention.

In the embodiment as shown wherein the head portion 40 is of a spherical shape for mating with the spherically shaped female seating portion 44, the configuration allows for up to 25° or more of angulation in all directions relative to the shaft portion 58 of the screw element 12". Thus, the present invention provides a multi-planar locking mechanism that allows for angulation in all planes. It also provides a locking mechanism that allows the mechanism to be locked at any angle prior to rod insertion. Further results of the above is that the invention provides a multi-planar locking mechanism that reduces intraoperative rod contouring provides flexibility.

With more specific regard to the locking mechanism, the sleeve ring 52 includes an edge surface 58. The nut member 26" includes an abutment surface 60 for abutting against the edge 58 as the nut member 26" is threaded onto the tapered threaded portion 24" to force the ring member 52 over the outer surface of the flanges 50.

In operation, the screw element 12" is fixed onto a bone, the head portion 40 extending from the bone surface. The rod seating member 14" is then disposed over the head portion 40 of the screw element 12" by insertion of the head portion 40 into the seat 44. This is a snapping operation but allows for angular adjustment of the tubular member 14" relative to the longitudinal axis of the screw element 12". The ring 52 is then disposed over the member 14" and an instrument is used to force the ring member 52 over the flanges 50 so as to lock the head portion 40 within the seat 44 thereby fixing the angulation between the two elements. The rod 20" is then seated within seat 16" of the member 14" as well as within the groove 54 of the ring 52. Finally, the nut member 26" is threaded over the tapered outer surface 24" of the arms 32",34" thereby fixing the rod 20" in frictional engagement within the seat 16" and against the nut member 26". Alternatively, as discussed above, the nut member 26" can be used to force the sleeve member 52 in place so as to lock the head 40 and screw member 12" relative to the element 14".

Utilizing the embodiment of the present invention as shown in FIGS. 1 and 2, the process is exactly the same with regard to locking the rod member 20 in place once the screw or hook portions 36,38, respectively, are connected to the known.

In view of the above, the present invention provides a method for locking a rod 20, 20" to a bone by the general steps of first fixing a rod seating member 14,14',14" to a bone and then seating a portion of the rod 20,20" within a substantially U-shaped seat 16,16" of the seating member 14,14',14". The rod 20,20" is locked within the U-shaped seat 16,16" while engaging and contouring at least a portion of the U-shaped seat 16,16" about the rod 20,20". As shown in FIGS. 3 and 4, this method can be more specifically defined by the steps of fixing the bone fixation member 12" to a bone and then locking and fixing the rod seating member 14" to the head portion 40 of the bone fixation member 12" and then locking the rod 20" within the U-shaped seat 16". The fixing step is accomplished by forcing the ring 52 over the outwardly flared portions 46 of the seat portion 44 to lock and fix the head portion 40 of the bone fixation element 12" therein. Finally, the locking of the rod is accomplished by locking the rod 20" within the U-shaped seat 16" by engaging the inner threaded surface 28" of the nut member 26" over the tapered outer threaded surface 24" of the U-shaped seat 16" to force the ring 52 over the outer surface 50 of the seat portion 44 to lock and fix the head portion 40 of the bone fixation element 12" therein while simultaneously deforming the inner surface of the U-shaped seat 16" about the rod 20" seated therein.

In accordance with this method, the locking mechanism is locked to the spherical head 40 of the bone fixation element 12" at a desired angle prior to rod insertion or locked simultaneously by tightening of the nut member 26". This locking method and the mechanism used therewith is fully reversible and top loading.

The invention has been described in an illustrative manner, and it is to be understood that the terminology which has been used is intended to be in the nature of words of description rather than of limitation.

Obviously, many modifications and variations of the present invention are possible in light of the above teachings. It is, therefore, to be understood that within the scope of the appended claims the invention may be practiced otherwise than as specifically describe.

What is claimed is:

1. A spinal implant fixation assembly (10) comprising: bone fixation means (12) for fixation of the assembly (10) to a support; rod receiving means (14) operatively connected to said bone fixation means (12) and including a first seat (16) having an inner wall (18) for seating a portion of a rod (20) therein, said rod receiving means (14) including a body portion (30) having two arms (32, 34) extending therefrom and being substantially parallel relative to each other, said two arms (32, 34) and body portion (30) forming a U-shaped inner surface (18) defining said first seat, and locking means (22) engaging said two arms (32, 34) for forcing, said first seat of said U-shaped inner surface (18) to contour around and engage the rod (20) seated therein and for locking and fixing the rod (20) relative to said assembly (10).

2. An assembly as set forth in claim 1 wherein said rod receiving means (14) includes a tapered outer surface (24), said locking means (22) including an inner surface for being forced over and engaging said outer tapered surface (24) and inwardly deflecting said rod receiving means (14) about said first seat (16) as said locking means (22) further engages said tapered outer surface (14).

3. An assembly as set forth in claim 2 wherein said tapered outer surface (24) is further defined as a tapered threaded surface (24), said locking means (22) including an inner threaded surface (20).

4. An assembly as set forth in claim 3 wherein said arms (32, 34) include said tapered threaded surface (24).

5. An assembly as set forth in claim 1 wherein said fixation means is further defined as bone fixation means for fixing said assembly (10) to a bone.

6. An assembly as set forth in claim 5 wherein said body portion (30) includes said bone fixation means (12) extending therefrom at a predetermined angle relative to said U-shaped inner surface (18) defining said first seat (16).

7. An assembly as set forth in claim 6 wherein said bone fixation means (12) includes a hook portion (38) extending from said body portion (30') and being integral therewith.

8. An assembly as set forth in claim 6 wherein said bone fixation means includes a screw portion (36) extending from said body portion (30) and being integral therewith.

9. An assembly as set forth in claim 5 wherein said bone fixation means (12") includes a head portion (40), said rod receiving means (14") including a second seat (44) for seating said head portion (40) therein, said second seat (44)

including an outer surface (50) thereabout, said locking means (22") including a skirt engaging and radially inwardly deflecting said outer surface of said second seat portion (42) for first locking and fixing said head portion (40) within said second seat (44) prior to said locking means (22") locking and fixing the rod (20") within the first seat (16").

10. An assembly as set forth in claim 9 wherein said rod receiving means (14") consists of a substantially tubular body including a pair of spaced, substantially parallel arms (32",34") extending therefrom and forming a substantially U-shaped seat defining said first seat (16"), said tubular body further including a socket portion including outwardly flaring flanges (46) having distal end portions flaring radially outwardly tapering surfaces (50) relative to a central axis of said rod receiving means defining said outer surface (50) of said second seat (44), said skirt portion (52) engaging and inwardly deflecting said distally outwardly tapering surfaces to engage said socket portion with said head portion (40).

11. An assembly as set forth in claim 10 wherein said locking means includes a ring member (52) defining said skirt portion, said tapered outer surface (24") of said rod receiving means (12") being a tapered threaded surface, said locking means (22") further including a nut member (26") including an inner threaded surface (28") for engaging and inwardly deflecting said tapered threaded surface (24").

12. An assembly as set forth in claim 11 wherein said head portion (40) is substantially spherical, said socket portion being substantially spherical for seating and engaging said head portion (40) therein.

13. An assembly as set forth in claim 11 wherein said ring (52) includes an edge surface (58), said nut member (26") including an abutment surface (60) for abutting against said edge surface (58) as said nut member (26") is threaded onto said tapered threaded portion (24") to force said ring member (52) over said outer surface of said socket portion.

14. A method for locking a rod (20,20") to a bone by fixing a rod seating member (14,14'14") to a bone; seating a portion of a rod (20,20") within a substantially U-shaped seat (16,16") of the seating member (14,14'14"), and locking the rod (20,20") within the U-shaped seat (16,16") directly while engaging and contouring at least a portion of the U-shaped seat (16,16") about the rod (20,20").

15. A method as set forth in claim 14 further including the steps of fixing a bone fixation member (12") to a bone; locking and fixing a rod seating member (14") to a head portion (40) of the bone fixation member (12"), and then locking the rod (20") within the U-shaped seat (16").

16. A method as set forth in claim 15 wherein said locking and fixing step is further defined as forcing a ring member (52) over an outwardly flared portion (46) of a seat portion (44) to lock and fix the head portion (40) of the bone fixation member (12") therein.

17. A method as set forth in claim 15 wherein said step of locking the rod (20") within the U-shaped seat (16") is further defined as enlarging an inner threaded surface (28") of a nut member (26") over a tapered outer threaded surface (24") of the U-shaped seat (16") to force the ring (52) over the outer surface (50) of the seat portion (44) to lock and fix the head portion (40) of the bone fixation member (12") therein while simultaneously deforming the inner surface of the U-shaped seat (16") about the rod (20") seated therein.

* * * * *